(12) United States Patent
Brogan et al.

(10) Patent No.: US 7,837,719 B2
(45) Date of Patent: Nov. 23, 2010

(54) ELECTRICAL STIMULATION UNIT AND WATERBATH SYSTEM

(75) Inventors: Michael S. Brogan, Buffalo, NY (US); Laura E. Edsberg, Newfane, NY (US); Douglas P. Kalinowski, Newstead, NY (US)

(73) Assignee: Daemen College, Amherst, NY (US)

( * ) Notice: Subject to any disclaimer, the term of this patent is extended or adjusted under 35 U.S.C. 154(b) by 124 days.

(21) Appl. No.: 10/513,555

(22) PCT Filed: May 9, 2003

(86) PCT No.: PCT/US03/14780

§ 371 (c)(1), (2), (4) Date: Nov. 5, 2004

(87) PCT Pub. No.: WO03/095018

PCT Pub. Date: Nov. 20, 2003

(65) Prior Publication Data

US 2005/0149124 A1    Jul. 7, 2005

(51) Int. Cl.
*A61N 1/44* (2006.01)
(52) U.S. Cl. .......................... 607/86; 607/50
(58) Field of Classification Search .............. 607/2, 607/3, 50, 144, 85–86
See application file for complete search history.

(56) References Cited

U.S. PATENT DOCUMENTS

| | | |
|---|---|---|
| 1,636,568 A * | 7/1927 | Kennedy ........................ 607/1 |
| 2,413,002 A | 12/1946 | Schurtz |
| 2,580,232 A | 12/1951 | Landaeur |
| 2,801,634 A | 8/1957 | De St. Cyr |
| 3,366,110 A | 1/1968 | Gaylord |
| 3,499,437 A | 3/1970 | Balamuth |
| 3,724,467 A | 4/1973 | Avery |
| 3,776,223 A | 12/1973 | Yeager |
| 3,881,495 A | 5/1975 | Pannozzo |
| 3,938,526 A | 2/1976 | Anderson |
| 3,989,050 A | 11/1976 | Buchalter |
| 4,453,548 A | 6/1984 | Maurer |
| 4,614,193 A | 9/1986 | Liss |
| 4,671,285 A | 6/1987 | Walker |
| 4,786,277 A * | 11/1988 | Powers et al. .................. 604/20 |
| 4,796,631 A | 1/1989 | Grigoryev |
| 4,846,181 A * | 7/1989 | Miller ......................... 607/50 |

(Continued)

FOREIGN PATENT DOCUMENTS

| | | |
|---|---|---|
| WO | 98/29157 | 7/1998 |
| WO | 2008041218 | 4/2008 |

OTHER PUBLICATIONS

Kalinowski et al. The Use of Low Voltage Direct Current as a Fungicidal Agent to Control the in vitro Growth of Trichophyton Mentagrophytes . . . Presented Apr. 28, 2003.

(Continued)

*Primary Examiner*—Carl H Layno
*Assistant Examiner*—Joseph Stoklosa
(74) *Attorney, Agent, or Firm*—Lando & Anastasi, LLP (57) ABSTRACT

A method for treating an infected area on a subject, comprising the steps of: exposing the infected area to an aqueous solution; and providing direct current to the aqueous solution to treat the infected area.

8 Claims, 2 Drawing Sheets

U.S. PATENT DOCUMENTS

| | | |
|---|---|---|
| 5,178,134 A | 1/1993 | Vago |
| 5,224,927 A * | 7/1993 | Tapper ........................ 604/20 |
| 5,231,988 A | 8/1993 | Wernicke |
| 5,256,137 A | 10/1993 | Sage |
| 5,263,481 A | 11/1993 | Axelgaard |
| 5,269,746 A | 12/1993 | Jacobson |
| 5,330,515 A | 7/1994 | Rutecki |
| 5,339,804 A | 8/1994 | Kemp |
| 5,387,231 A | 2/1995 | Sporer |
| 5,514,175 A | 5/1996 | Kim |
| 5,540,734 A | 7/1996 | Zabara |
| 5,571,118 A | 11/1996 | Boutos |
| 5,693,004 A | 12/1997 | Carlson |
| 5,697,966 A | 12/1997 | Boutos |
| 5,741,317 A * | 4/1998 | Ostrow ........................ 607/85 |
| 5,776,170 A | 7/1998 | MacDonald |
| 5,782,902 A | 7/1998 | Boutos |
| 5,785,040 A | 7/1998 | Axelgaard |
| 5,800,502 A | 9/1998 | Boutos |
| 5,851,223 A | 12/1998 | Liss |
| 5,871,533 A | 2/1999 | Boutos |
| 5,983,134 A | 11/1999 | Ostrow |
| 6,002,964 A | 12/1999 | Feler |
| 6,004,257 A | 12/1999 | Jacobson |
| 6,016,451 A | 1/2000 | Sanchez-Rodarte |
| 6,023,640 A | 2/2000 | Ross |
| 6,027,496 A | 2/2000 | Loomis |
| 6,049,927 A | 4/2000 | Thomas |
| 6,058,331 A | 5/2000 | King |
| 6,063,108 A | 5/2000 | Salansky |
| 6,078,842 A * | 6/2000 | Gross et al. ................ 607/152 |
| 6,094,533 A | 7/2000 | Allen |
| 6,128,536 A | 10/2000 | Noack |
| 6,156,007 A | 12/2000 | Ash |
| 6,179,797 B1 | 1/2001 | Brotz |
| 6,182,316 B1 | 2/2001 | Thomas |
| 6,230,052 B1 | 5/2001 | Wolff |
| 6,245,060 B1 | 6/2001 | Loomis |
| 6,264,680 B1 | 7/2001 | Ash |
| 6,302,900 B1 | 10/2001 | Riggs |
| 6,317,629 B1 | 11/2001 | Haak |
| 6,330,471 B1 * | 12/2001 | Higo et al. .................. 604/20 |
| 6,351,672 B1 | 2/2002 | Park |
| 6,366,802 B1 | 4/2002 | Haber |
| 6,425,877 B1 | 7/2002 | Edwards |
| 6,436,060 B1 | 8/2002 | Talish |
| 6,453,204 B1 | 9/2002 | Rhodes |
| 6,466,821 B1 | 10/2002 | Pianca |
| 6,477,406 B1 | 11/2002 | Turcott |
| 6,494,900 B1 | 12/2002 | Salansky |
| 6,575,892 B1 | 6/2003 | Lauter |
| 6,606,519 B2 | 8/2003 | Powell |
| 6,607,550 B1 | 8/2003 | Bertwell |
| 6,622,041 B2 | 9/2003 | Terry |
| 6,650,932 B1 | 11/2003 | Cohen |
| 6,650,943 B1 | 11/2003 | Whitehurst |
| 6,721,603 B2 | 4/2004 | Zabara |
| 6,735,481 B1 | 5/2004 | Bingham |
| 6,745,078 B1 | 6/2004 | Buchner |
| 6,751,506 B2 | 6/2004 | Shealy |
| 6,788,976 B2 | 9/2004 | Gesotti |
| 6,853,865 B2 | 2/2005 | Beens |
| 6,862,479 B1 | 3/2005 | Whitehurst |
| 6,871,092 B2 | 3/2005 | Piccone |
| 6,871,099 B1 | 3/2005 | Whitehurst |
| 6,885,895 B1 | 4/2005 | Whitehurst |
| 6,937,900 B1 | 8/2005 | Pianca |
| 6,942,658 B1 | 9/2005 | Rizoiu |
| 6,970,741 B1 | 11/2005 | Whitehurst |
| 6,978,180 B2 | 12/2005 | Tadlock |
| 6,990,376 B2 | 1/2006 | Tanagho |
| 7,006,870 B1 | 2/2006 | Whitehurst |
| 7,010,353 B2 | 3/2006 | Gan |
| 7,013,177 B1 | 3/2006 | Whitehurst |
| 7,033,329 B2 | 4/2006 | Liao |
| 7,117,034 B2 | 10/2006 | Kronberg |
| 7,146,209 B2 | 12/2006 | Gross |
| 7,150,710 B2 | 12/2006 | Haber |
| 7,156,866 B1 | 1/2007 | Riggs |
| 7,160,434 B2 | 1/2007 | Becker |
| 7,167,750 B2 | 1/2007 | Knudson |
| 7,203,548 B2 | 4/2007 | Whitehurst |
| 7,206,632 B2 | 4/2007 | King |
| 7,209,791 B2 | 4/2007 | Odom |
| 7,225,023 B1 | 5/2007 | Park |
| 7,229,468 B2 | 6/2007 | Wong |
| 7,239,918 B2 | 7/2007 | Strother |
| 7,258,658 B2 | 8/2007 | Pasula |
| 7,292,890 B2 | 11/2007 | Whitehurst |
| 7,337,005 B2 | 2/2008 | Kim |
| 7,337,006 B2 | 2/2008 | Kim |
| 7,338,480 B2 | 3/2008 | Nakajima |
| 7,341,597 B2 | 3/2008 | Tucek |
| 7,349,743 B2 | 3/2008 | Tadlock |
| 7,369,896 B2 | 5/2008 | Gesotti |
| 7,384,419 B2 | 6/2008 | Jones |
| 7,386,347 B2 | 6/2008 | Chung |
| 7,402,167 B2 | 7/2008 | Nemenov |
| 7,440,806 B1 | 10/2008 | Whitehurst |
| 7,444,183 B2 | 10/2008 | Knudson |
| 7,447,546 B2 | 11/2008 | Kim |
| 7,450,993 B2 | 11/2008 | Kim |
| 2001/0039441 A1 | 11/2001 | Ash |
| 2002/0072780 A1 | 6/2002 | Foley |
| 2002/0165591 A1 | 11/2002 | Piccone |
| 2002/0173828 A1 | 11/2002 | Gozani |
| 2003/0040774 A1 | 2/2003 | Terry |
| 2003/0088294 A1 | 5/2003 | Gesotti |
| 2003/0111084 A1 | 6/2003 | Revazova |
| 2003/0120322 A1 | 6/2003 | Benja-Athon |
| 2003/0130707 A1 | 7/2003 | Gan |
| 2003/0130709 A1 | 7/2003 | D.C. |
| 2003/0144625 A1 | 7/2003 | Sherman |
| 2003/0144709 A1 | 7/2003 | Zabara |
| 2003/0176898 A1 | 9/2003 | Gross |
| 2003/0220668 A1 | 11/2003 | Shealy |
| 2003/0236557 A1 | 12/2003 | Whitehurst |
| 2003/0236558 A1 | 12/2003 | Whitehurst |
| 2004/0015202 A1 | 1/2004 | Chandler |
| 2004/0015204 A1 | 1/2004 | Whitehurst |
| 2004/0015205 A1 | 1/2004 | Whitehurst |
| 2004/0039417 A1 | 2/2004 | Soykan |
| 2004/0044386 A1 | 3/2004 | Beens |
| 2004/0087883 A1 | 5/2004 | Berger |
| 2004/0088025 A1 | 5/2004 | Gesotti |
| 2004/0111126 A1 | 6/2004 | Tanagho |
| 2004/0138708 A1 * | 7/2004 | Tucek ........................ 607/2 |
| 2004/0158300 A1 | 8/2004 | Gardiner |
| 2004/0162583 A1 | 8/2004 | Bingham |
| 2004/0162595 A1 | 8/2004 | Foley |
| 2004/0167583 A1 | 8/2004 | Knudson |
| 2004/0172085 A1 | 9/2004 | Knudson |
| 2004/0172086 A1 | 9/2004 | Knudson |
| 2004/0172088 A1 | 9/2004 | Knudson |
| 2004/0176812 A1 | 9/2004 | Knudson |
| 2004/0186532 A1 | 9/2004 | Tadlock |
| 2004/0210290 A1 | 10/2004 | Omar-Pasha |
| 2004/0215293 A1 | 10/2004 | Eells |
| 2004/0230226 A1 | 11/2004 | Bingham |
| 2004/0230252 A1 | 11/2004 | Kullok |
| 2004/0243206 A1 | 12/2004 | Tadlock |
| 2004/0249429 A1 | 12/2004 | Tadlock |
| 2004/0254567 A1 | 12/2004 | Holz |
| 2004/0267333 A1 | 12/2004 | Kronberg |

| | | | | | |
|---|---|---|---|---|---|
| 2005/0027336 A1 | 2/2005 | Nemenov | 2007/0021800 A1 | 1/2007 | Whitehurst |
| 2005/0033387 A1 | 2/2005 | Buchner | 2007/0021803 A1 | 1/2007 | Deem |
| 2005/0038375 A1 | 2/2005 | Nitzan | 2007/0038273 A1 | 2/2007 | Bales |
| 2005/0043773 A1 | 2/2005 | Lieberburg | 2007/0043408 A1 | 2/2007 | Winnett |
| 2005/0059148 A1 | 3/2005 | Kubota | 2007/0060862 A1 | 3/2007 | Sun |
| 2005/0059153 A1 | 3/2005 | George | 2007/0060955 A1 | 3/2007 | Strother |
| 2005/0065553 A1 | 3/2005 | Ben Ezra | 2007/0060968 A1 | 3/2007 | Strother |
| 2005/0075669 A1 | 4/2005 | King | 2007/0060979 A1 | 3/2007 | Strother |
| 2005/0119713 A1 | 6/2005 | Whitehurst | 2007/0060980 A1 | 3/2007 | Strother |
| 2005/0137667 A1 | 6/2005 | Omar-Pasha | 2007/0066995 A1 | 3/2007 | Strother |
| 2005/0143789 A1 | 6/2005 | Whitehurst | 2007/0067000 A1 | 3/2007 | Strother |
| 2005/0149124 A1 | 7/2005 | Brogan et al. | 2007/0073353 A1 | 3/2007 | Rooney |
| 2005/0154418 A1 | 7/2005 | Kieval | 2007/0073356 A1 | 3/2007 | Rooney |
| 2005/0159790 A1 | 7/2005 | Shalev | 2007/0073357 A1 | 3/2007 | Rooney |
| 2005/0177215 A1 | 8/2005 | Rosenberg | 2007/0073361 A1 | 3/2007 | Goren |
| 2005/0197675 A1 | 9/2005 | David | 2007/0088392 A1 | 4/2007 | Skiba |
| 2005/0203578 A1 | 9/2005 | Weiner | 2007/0088407 A1 | 4/2007 | Smith |
| 2005/0203585 A1 | 9/2005 | Hairfield | 2007/0093878 A1 | 4/2007 | Edge |
| 2005/0209652 A1 | 9/2005 | Whitehurst | 2007/0104664 A1 | 5/2007 | Maltezos |
| 2005/0222651 A1 | 10/2005 | Jung | 2007/0123758 A1 | 5/2007 | Miesel |
| 2005/0234525 A1 | 10/2005 | Phillips | 2007/0123844 A1 | 5/2007 | Henry |
| 2005/0240229 A1 | 10/2005 | Whitehurst | 2007/0129771 A1 | 6/2007 | Kurtz |
| 2005/0240253 A1 | 10/2005 | Tyler | 2007/0135846 A1 | 6/2007 | Knudson |
| 2005/0256552 A1 | 11/2005 | White | 2007/0135856 A1 | 6/2007 | Knudson |
| 2005/0267542 A1 | 12/2005 | David | 2007/0135857 A1 | 6/2007 | Knudson |
| 2005/0277999 A1 | 12/2005 | Strother | 2007/0135858 A1 | 6/2007 | Knudson |
| 2005/0278000 A1 | 12/2005 | Strother | 2007/0142870 A1 | 6/2007 | Knudson |
| 2006/0004422 A1 | 1/2006 | De Ridder | 2007/0150034 A1 | 6/2007 | Rooney |
| 2006/0004431 A1 | 1/2006 | Fuller | 2007/0156208 A1 | 7/2007 | Havell |
| 2006/0009805 A1 | 1/2006 | Jensen | 2007/0162093 A1 | 7/2007 | Porter |
| 2006/0020291 A1 | 1/2006 | Gozani | 2007/0167999 A1 | 7/2007 | Breden |
| 2006/0020299 A1 | 1/2006 | Shalev | 2007/0173892 A1 | 7/2007 | Fleischer |
| 2006/0030907 A1 | 2/2006 | McNew | 2007/0173903 A1 | 7/2007 | Goren |
| 2006/0036286 A1 | 2/2006 | Whitehurst | 2007/0179533 A1 | 8/2007 | Baugh |
| 2006/0036298 A1 | 2/2006 | Smith | 2007/0185553 A1 | 8/2007 | Kennedy |
| 2006/0047326 A1 | 3/2006 | Wheeler | 2007/0203432 A1 | 8/2007 | McNew |
| 2006/0052826 A1 | 3/2006 | Kim | 2007/0203533 A1 | 8/2007 | Goren |
| 2006/0052827 A1 | 3/2006 | Kim | 2007/0225769 A1 | 9/2007 | Smith |
| 2006/0052828 A1 | 3/2006 | Kim | 2007/0237797 A1 | 10/2007 | Peyman |
| 2006/0052835 A1 | 3/2006 | Kim | 2007/0239212 A1 | 10/2007 | Schneider |
| 2006/0052836 A1 | 3/2006 | Kim | 2007/0239243 A1 | 10/2007 | Moffitt |
| 2006/0052837 A1 | 3/2006 | Kim | 2007/0249968 A1 | 10/2007 | Miesel |
| 2006/0052838 A1 | 3/2006 | Kim | 2007/0250119 A1 | 10/2007 | Tyler |
| 2006/0052839 A1 | 3/2006 | Kim | 2007/0250121 A1 | 10/2007 | Miesel |
| 2006/0052845 A1 | 3/2006 | Zanella | 2007/0250134 A1 | 10/2007 | Miesel |
| 2006/0052856 A1 | 3/2006 | Kim | 2007/0255379 A1 | 11/2007 | Williams |
| 2006/0063963 A1 | 3/2006 | Brunelle | 2007/0260291 A1 | 11/2007 | Hunter |
| 2006/0064139 A1 | 3/2006 | Chung | 2007/0260297 A1 | 11/2007 | Chariff |
| 2006/0095088 A1 | 5/2006 | De Ridder | 2007/0276439 A1 | 11/2007 | Miesel |
| 2006/0100668 A1 | 5/2006 | Ben-David | 2007/0282228 A1 | 12/2007 | Einav |
| 2006/0100671 A1 | 5/2006 | Ridder | 2007/0282378 A1 | 12/2007 | Huang |
| 2006/0111754 A1 | 5/2006 | Rezai | 2007/0282405 A1 | 12/2007 | Wong |
| 2006/0136008 A1 | 6/2006 | Tadlock | 2007/0293906 A1 | 12/2007 | Cowan |
| 2006/0136022 A1 | 6/2006 | Wong | 2007/0293909 A1 | 12/2007 | Cowan |
| 2006/0149333 A1 | 7/2006 | Tanagho | 2007/0293910 A1 | 12/2007 | Strother |
| 2006/0149345 A1 | 7/2006 | Boggs | 2007/0299483 A1 | 12/2007 | Strother |
| 2006/0155340 A1 | 7/2006 | Schuler | 2008/0004672 A1 | 1/2008 | Dalal |
| 2006/0155345 A1 | 7/2006 | Williams | 2008/0004674 A1 | 1/2008 | King |
| 2006/0161218 A1 | 7/2006 | Danilov | 2008/0004675 A1 | 1/2008 | King |
| 2006/0173507 A1 | 8/2006 | Mrva | 2008/0004677 A1 | 1/2008 | Gay |
| 2006/0178705 A1 | 8/2006 | Janssen | 2008/0015640 A1 | 1/2008 | Kaiser |
| 2006/0184214 A1 | 8/2006 | McDaniel | 2008/0021512 A1 | 1/2008 | Knudson |
| 2006/0206155 A1 | 9/2006 | Ben-David | 2008/0027519 A1 | 1/2008 | Guerrero |
| 2006/0206159 A1 | 9/2006 | Moffitt | 2008/0039904 A1 | 2/2008 | Bulkes |
| 2006/0224215 A1 | 10/2006 | Pattern | 2008/0046036 A1 | 2/2008 | King |
| 2006/0241718 A1 | 10/2006 | Tyler | 2008/0051858 A1 | 2/2008 | Haber |
| 2006/0264804 A1 | 11/2006 | Karmon | 2008/0065167 A1 | 3/2008 | Boggs |
| 2006/0265029 A1 | 11/2006 | Huang | 2008/0065183 A1 | 3/2008 | Whitehurst |
| 2006/0270944 A1 | 11/2006 | King | 2008/0071321 A1 | 3/2008 | Boggs |
| 2006/0276741 A1 | 12/2006 | Henley | 2008/0071324 A1 | 3/2008 | Miesel |
| 2006/0282134 A1 | 12/2006 | Shapiro | 2008/0071326 A1 | 3/2008 | Heruth |
| 2006/0293726 A1 | 12/2006 | Odom | 2008/0071327 A1 | 3/2008 | Miesel |
| 2007/0010860 A1 | 1/2007 | Gafni | 2008/0071333 A1 | 3/2008 | Hayes |

| | | |
|---|---|---|
| 2008/0076958 A1 | 3/2008 | Britva |
| 2008/0086182 A1 | 4/2008 | Ben-David |
| 2008/0087288 A1 | 4/2008 | Wun |
| 2008/0091240 A1 | 4/2008 | Ben-David |
| 2008/0103534 A1 | 5/2008 | Gerber |
| 2008/0103569 A1 | 5/2008 | Gerber |
| 2008/0103570 A1 | 5/2008 | Gerber |
| 2008/0103572 A1 | 5/2008 | Gerber |
| 2008/0103573 A1 | 5/2008 | Gerber |
| 2008/0103574 A1 | 5/2008 | Gerber |
| 2008/0103575 A1 | 5/2008 | Gerber |
| 2008/0103576 A1 | 5/2008 | Gerber |
| 2008/0103577 A1 | 5/2008 | Gerber |
| 2008/0103578 A1 | 5/2008 | Gerber |
| 2008/0103579 A1 | 5/2008 | Gerber |
| 2008/0103580 A1 | 5/2008 | Gerber |
| 2008/0108579 A1 | 5/2008 | Peyman |
| 2008/0119898 A1 | 5/2008 | Ben-David |
| 2008/0125819 A1 | 5/2008 | Ben-David |
| 2008/0125843 A1 | 5/2008 | Ben-David |
| 2008/0132933 A1 | 6/2008 | Gerber |
| 2008/0132961 A1 | 6/2008 | Jaax |
| 2008/0132974 A1 | 6/2008 | Strother |
| 2008/0132980 A1 | 6/2008 | Gerber |
| 2008/0132981 A1 | 6/2008 | Gerber |
| 2008/0132982 A1 | 6/2008 | Gerber |
| 2008/0140141 A1 | 6/2008 | Ben-David |
| 2008/0140161 A1 | 6/2008 | Goetz |
| 2008/0140162 A1 | 6/2008 | Goetz |
| 2008/0140163 A1 | 6/2008 | Keacher |
| 2008/0161874 A1 | 7/2008 | Bennett |
| 2008/0161894 A1 | 7/2008 | Ben-David |
| 2008/0167698 A1 | 7/2008 | Kim |
| 2008/0172104 A1 | 7/2008 | Kieval |
| 2008/0208280 A1 | 8/2008 | Lindenthaler |
| 2008/0208286 A1 | 8/2008 | Kieval |
| 2008/0208288 A1 | 8/2008 | Gesotti |
| 2008/0215101 A1 | 9/2008 | Rezai |
| 2008/0215115 A1 | 9/2008 | Bingham |
| 2008/0228239 A1 | 9/2008 | Tyler |
| 2008/0255476 A1 | 10/2008 | Boyajian |
| 2008/0269812 A1 | 10/2008 | Gerber |
| 2008/0269821 A1 | 10/2008 | Kullok |
| 2008/0269843 A1 | 10/2008 | Gerber |
| 2008/0269847 A1 | 10/2008 | Nemenov |
| 2008/0269849 A1 | 10/2008 | Lewis |
| 2008/0275514 A1 | 11/2008 | Ben-David |

OTHER PUBLICATIONS

Edsberg et al. In Vitro and In Vivo Outcomes with the Use of a New Anti-Fungal Device, presented Feb. 12, 2003.
Poster entitled "The Effects of High Voltage Electrical Stimulation and Hydrogen Peroxide in an Aqueous Solution on Subjects Between the Ages of 18-75 with Onychomycosis." Dec. 2004.
Kalinowski et al. "Low Voltage Direct Current as a Fungicidal Agent for Treating Onychomycosis." J. Amer. Pod. Med. Assoc., 94, 2004, pp. 565-572.
Kalinowski et al. "A Practical Technique for Disinfecting Electrical Stimulation Apparatuses Used in Wound Treatment." Physical therapy, 76, 1996, pp. 1340-1347.
Gonsiorek, E.A. "The Effects of Low Voltage Direct Current on Trichophyton Metagrophytes in vitro." Abstract. Physical Therapy. May 2000.
Brogan et al. "The Use of High Voltage Pulsed Current on a Case of an Open Wound Infected with MRSA and Underlying Osteomyelitis." NYPTA. Oct. 1996.
Jacques et al. "High Voltage Electrical Treatment of Refractory Dermal Ulcers." Physician Assistant. Mar. 1997, pp. 84-98.
Hulsheger et al. "Electric Effects on Bacteria and Yeast Cells." Radiat. and Environ. Biophysics. 22, 1983, pp. 149-163.
Szuminsky et al. "Effect of Narrow, Pulsed High Voltages on Bacterial Viability." Physical Therapy, 74, 1994, pp. 57-64.
Liu et al. "The Effects of Electric Current on Bacteria Colonising Intravenous Catheters." J. Infection. 27, 1993, pp. 261-269.
Kincaid and Lavoie. "Inhibition of Bacterial Growth In Vitro Following Stimulation with High Voltage, Monophasic Pulsed Current." Physical Therapy. 69, 1989, pp. 29-33.
Hulsheger et al. "Killing of Bacteria with Electric Pulses of High Field Strength." Radiat. Environ. Biophys. 20, 1981, pp. 53-65.

* cited by examiner

Figure 1. Electrical Stimulation Unit and Water Bath System

Figure 2: The Electrical Stimulation Unit and Garment System

ELECTRICAL STIMULATION UNIT AND WATERBATH SYSTEM

TECHNICAL FIELD

The present invention relates generally to the field of treating infections, and, more particularly, to an improved fungicidal/fungistatic treatment system for treating toenail fungus, dermatological fungi, fungal infections, and the like.

BACKGROUND ART

Toenail fungus alone affects 2-13% of the general population of the United States; over 30% of the population over 60 years of age are affected. Current systemic treatment consists of the use of an expensive drugs or pharmaceutical agents many of which have complications and associated interactions. These pharmaceutical treatments are less than ideal for many patients because of the cost and danger associated with them.

Various approaches to treating this disease have been attempted and employed, and most involve pharmaceutical agents applied topically or systematically. For instance, U.S. Pat. No. 6,319,957 describes the use of compositions based on glyco-alcohol, hydro-alcohol or glyco-hydro-alcohol solutions of a glycol or glyceric ester of retinoic acid, preferably in association with the ethyl ester of retinoic acid and with hydroquinone, treat unsightly skin disorders such as acne, wrinkles, scars, stretch marks, dark spots, etc., and in treating mycotic skin diseases and psoriasis.

U.S. Pat. No. 6,303,140 teaches a plaster preparation comprising a synthetic rubber; a reinforcing agent based on silica or random styrene-butadiene, copolymer; a tackifier; salicylic acid or a pharmaceutically acceptable salt or ester thereof to treat mycotic infections.

U.S. Pat. No. 6,290,950 describes a new class of mycosis vaccines comprising homogenised inactivated yeast blastospores and homogenised inactivated dermatophyte microconidia or antigenic material of said spores, methods for their production and their use for the prophylaxis and/or treatment of mycoses in mammals, preferably humans. The vaccines according to the present invention are especially useful for the prophylaxis and/or treatment of skin mycosis, preferably dermatomycosis and/or candidosis and/or onychomycosis.

U.S. Pat. No. 6,287,276 describes a set depth nail notcher and method for treating nail fungus that is used to cut a notch to a predetermined depth in a nail or a toe of finger infected with fungus and then apply a topical anti-fungal medication to the toe or finger through the notch.

U.S. Pat. No. 6,281,239 teaches a method of treating onychomycosis by administering to an infected area around a nail of a patient a tissue softening composition containing urea and an antifungal composition in one or separate compositions, concurrently or non-concurrently.

Several studies have reported that electrical stimulation augments wound healing, Electrical stimulation has been reported to improve blood flow, decrease edema, and inhibit bacterial growth. Numerous studies have reported that monophasic pulsed current from a high voltage pulsed source (HVPC) augments wound healing. Additional studies have shown significant increases in transcutaneous partial pressure of oxygen ($tCP\ O_2$) in diabetic individuals following use of electrical stimulation. HVPC has been used to successfully treat diabetic foot ulcers.

Several studies have demonstrated that electrical currents exist in living organisms. Cells follow the path of this current flow, which is referred to as the galvanotaxic effect. It is theorized that electrical stimulation augments the endogenous bioelectric system in the body. The increase in the rate of wound healing with electrical stimulation is also theorized to be a result of attraction of different cell types. Studies have shown that migration of macrophages, fibroblasts, mast cells, neutrophils, and epidermal cells is influenced by electrical stimulation. Electrical stimulation has also been shown to increase the proliferation of fibroblasts and protein synthesis, as well as the growth of neurites. These factors play a significant role in healing. Furthermore, the tensile strength of the collagen has been shown to increase upon application of such electrical fields, thus increasing the strength of the wound scars. For these reasons, the use of electrical stimulation for the treatment of chronic wounds has been used increasingly during the last several years.

The term onychomycosis refers to any fungal infection of one or more elements of the nail system, which consists of the nail matrix, the nail bed and the nail plate. Several studies suggest that onychomycosis affects between 2% and 18% (or possibly more) of the world's population. In North America, onychomycosis accounts for approximately 50% of all nail disease, is an infection several times more common in the toenail than the fingernail, and is most commonly found among older individuals. Some studies suggest that nearly 50% of the population over 70 years of age may be affected. The incidence of onychomycosis in the United States and other countries of the developed world has been increasing in recent years. This is thought to be most likely the result of several contributing factors including: the general aging of the population; the possible higher incidence of diabetes mellitus; the greater use of immunosuppressive drugs and antibiotics; the increased exposure of the general population to the etiologic fungi; the HIV epidemic.

Onychomycosis can be caused by three different groups of fungi: the dermatophytes, the yeasts and the nondermatophytic molds. The dermatophytes are the most common etiology, accounting for between 85% and 90% of all cases. Just two dermatophyte species, *Trichophyton rubrum* (*T. rubrum*) and *Trichophyton mentagrophytes* (*T. mentagrophyte*), are responsible themselves for nearly 80% of all cases of onychomycosis. Several different yeast species can also cause onychomycosis. These species are together responsible for between 5% and 10% all cases. In approximately 70% of these cases, the etiological agent is *Candida albicans*. Finally, several different species of the nondermatophyte molds can also cause onychomycosis. As a group, these are responsible for approximately 3% to 5% of all cases.

Although onychomycosis is not a fatal infection, and is usually not a very debilitating condition in most afflicted individuals, it can still have serious emotional and/or physical consequences. The condition can be associated with significant pain and discomfort, and in severe cases, it may sometimes lead to disfigurement and/or to various degrees of functional loss. In addition to physical impairment, the psychological and social consequences of onychomycosis can also be significant. Thus, onychomycosis represents far more than a mere cosmetic problem for many afflicted individuals, and professional treatment from health care providers is very often sought.

The treatment of onychomycosis, however, has proven difficult. The three traditional approaches to treatment are debridement of the nail unit, topical medication and systemic chemotherapy. The most successful of these approaches has been the use of systemic antifungal drugs. Over the last 40 years, oral systemic antifungal agents have been the mainstay of onychomycosis therapy. However, because of several negative factors that include drug toxicity, possible adverse interactions of antifungal agents with other drugs in the body, and the prolonged course of treatment required with many of these antifungal therapeutic regimes, the search for new, alternative treatments, which are both efficacious and which present minimal side effects, is still an important research goal.

DISCLOSURE OF THE INVENTION

With parenthetical reference to the corresponding parts, portions and surfaces of the disclosed embodiment, merely for purposes of illustration and not by way of limitation, the present invention broadly provides a method and apparatus for treating infections in human or animal subjects.

In one aspect, the invention provides a method for treating an infected area on a subject, comprising the steps of exposing the infected area to an aqueous solution; and providing direct current to the aqueous solution to treat the infected area. This method of treatment may also be used to treat other infections including onchomycosis, molluscum contagium, papilloma virus, warts, epidermodysplasia verruciformis, herpes virus, or other fungal infection. The method may be used to treat an infected area wherein the infected area is on the skin of the subject.

In another aspect of the invention, the aqueous solution includes hydrogen peroxide. Another aspect is where the aqueous solution comprises about 0.01 to 3.0 weight percent hydrogen peroxide.

It is an object of the invention to provide direct current of less than about 3 milliamperes, or less than about 50 milliamperes. It is another object of the invention to provide direct current supplied by a voltage source of less than about 150 volts. In another aspect of the invention the direct current is pulsed. In another aspect, the direct current has a pulse width of about 5-50 microseconds. In yet another aspect of this invention, the infected area is treated with the direct current for a time period of about 20-45 minutes.

This invention also relates to apparatus for treating an infected area on a subject comprising: a reservoir; an aqueous solution in the reservoir and exposed to the infected area; a first electrode in the reservoir; a second electrode in the reservoir; and a circuit for providing current to the aqueous solution to treat the infected area.

In one aspect the infected area is immersed in the aqueous solution.

In another aspect, the first electrode and second electrode are formed of stainless steel.

It is an object of this invention to provide a wearable apparatus for the treatment an infected area on a subject comprising a membrane made of a material that is impervious to aqueous solutions and having a periphery or an edge; an adhesive disposed on the periphery or edge of the membrane; an aqueous solution in the membrane in contact with an infected area of a subject; a first electrode affixed to the membrane; a second electrode affixed to the membrane; and a circuit for providing current to the aqueous solution to treat the infected area.

It is a further object of the invention to provide such apparatus with a liquid filler opening that allows the apparatus to be placed against the infected area to form a pocket which is capable of holding an amount of an aqueous solution.

It is also an object of the invention to provide such apparatus where the membrane is adapted to be attached to the subject.

In another aspect of the invention, the first electrode and second electrode are formed of stainless steel.

DESCRIPTION OF THE PREFERRED EMBODIMENTS

Both monophasic pulsed current from a high voltage source (HVPC) and direct current electrical stimulation from a low voltage source (LVDC) are fungicidal/fungistatic. Humans treated with HVPC electrical stimulation in a waterbath displayed markedly diminished fungal infection, and sound normal nail growth. The growth of *Trichophyton meiitagrophytes* fungi and *Trichophyton rubru* fungi can be inhibited with direct current electrical stimulation from a low voltage source. The fungicidal/fungistatic properties of electrical stimulation on toenail fungus, dermatological fungi, and other fungal infections has been demonstrated.

EXAMPLE 1

Based on these experiments and the discovery of electrical stimulation's fungicidal/fungistatic properties, it is logical that a therapeutic device could be fashioned consisting of a small electrical stimulation unit and a foot waterbath system. Referring now to the drawings, and, more particularly, to FIG. 1 thereof, an appliance used to treat toenail fungus will comprise a waterbath (1) designed to allow either one or both feet (2) to fit comfortably and be immersed in solution (3). An electrode (4) on either side of the bath will allow a safe current to pass through the solution (3) and over and around the toes and the nails. The current will be supplied by an electrical stimulation unit (5), which will be a small device easily attachable to, or built into, the bath (1). The electrical stimulation unit (5) will have leads, which attach to the electrodes (4). The system used to treat toenail fungus will have leads on either side of the bath, lateral and medial or front and back. The therapeutic device will be adapted to treating other parts of the body which can be easily immersed, for example, hands.

Figure 1:
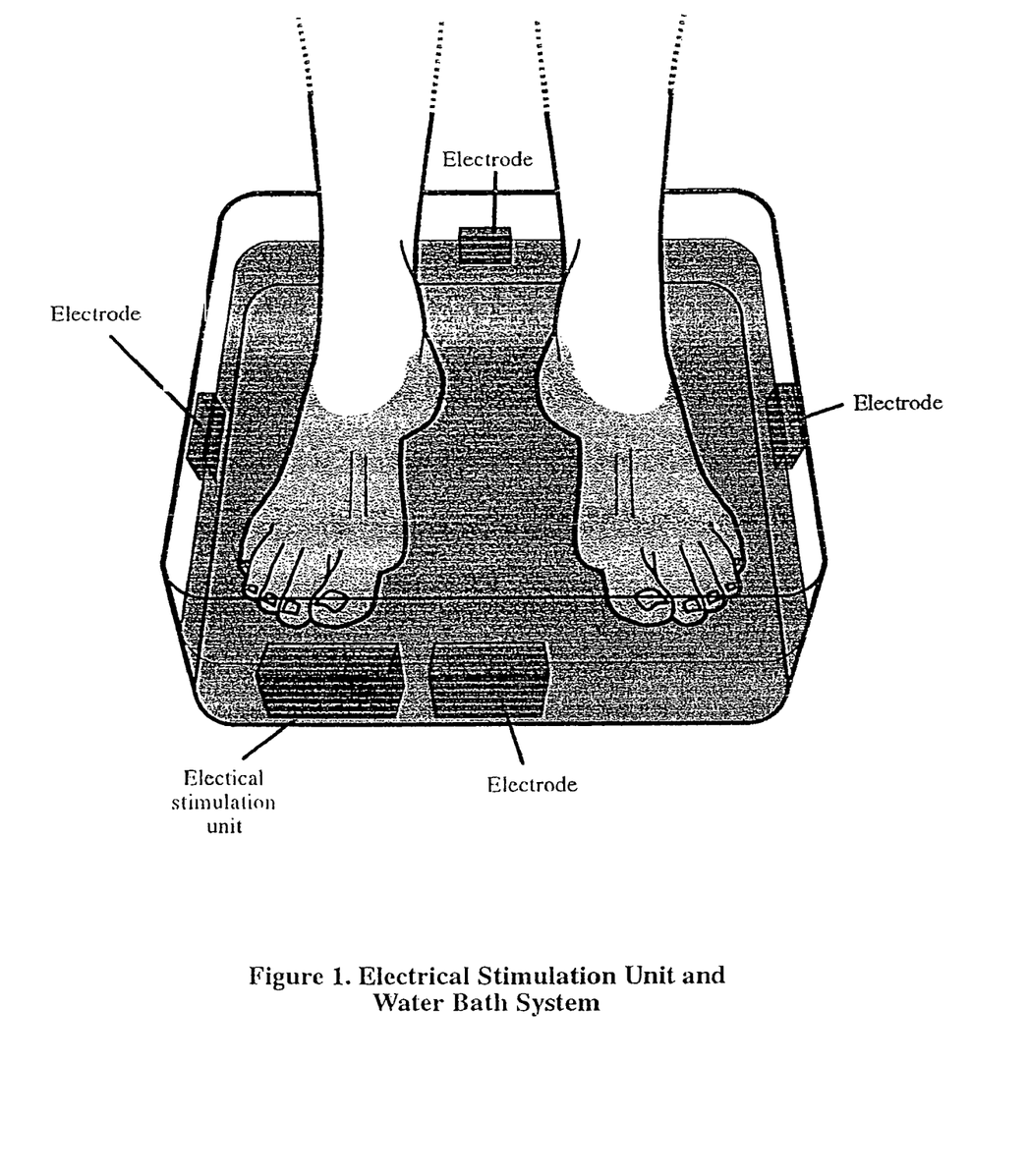
FIG. 1 shows a subject's infected area immersed in a reservoir with a source of high or low voltage current available.

The device delivers a pulsed current of 0 to 150 volts at peak in pulse pairs of 150-330 microseconds apart. The pulse width is 5-50 microseconds and the pair repeat frequency is 100-200 Hz. This device is connected to the waterbath by way of electrodes, thus allowing electrical current to travel in the solution and cover the affected area. This unit will be as safe as a transcutaneous electrical nerve stimulator (TENS) unit presently used for pain modulation, but will be potentiated to deliver a distinct type of current.

Based on findings of the fungicidal/fungistatic properties of both pulsed and direct current electrical stimulation, many additional applications are possible. In addition to toe nail fungus, dermatological fungi, fungi in wounds and fungal infections are additional fungi, which could be treated with this system. Also, veterinary applications are possible for animals and livestock with fungal infections are anticipated.

EXAMPLE 2

Figure 2:
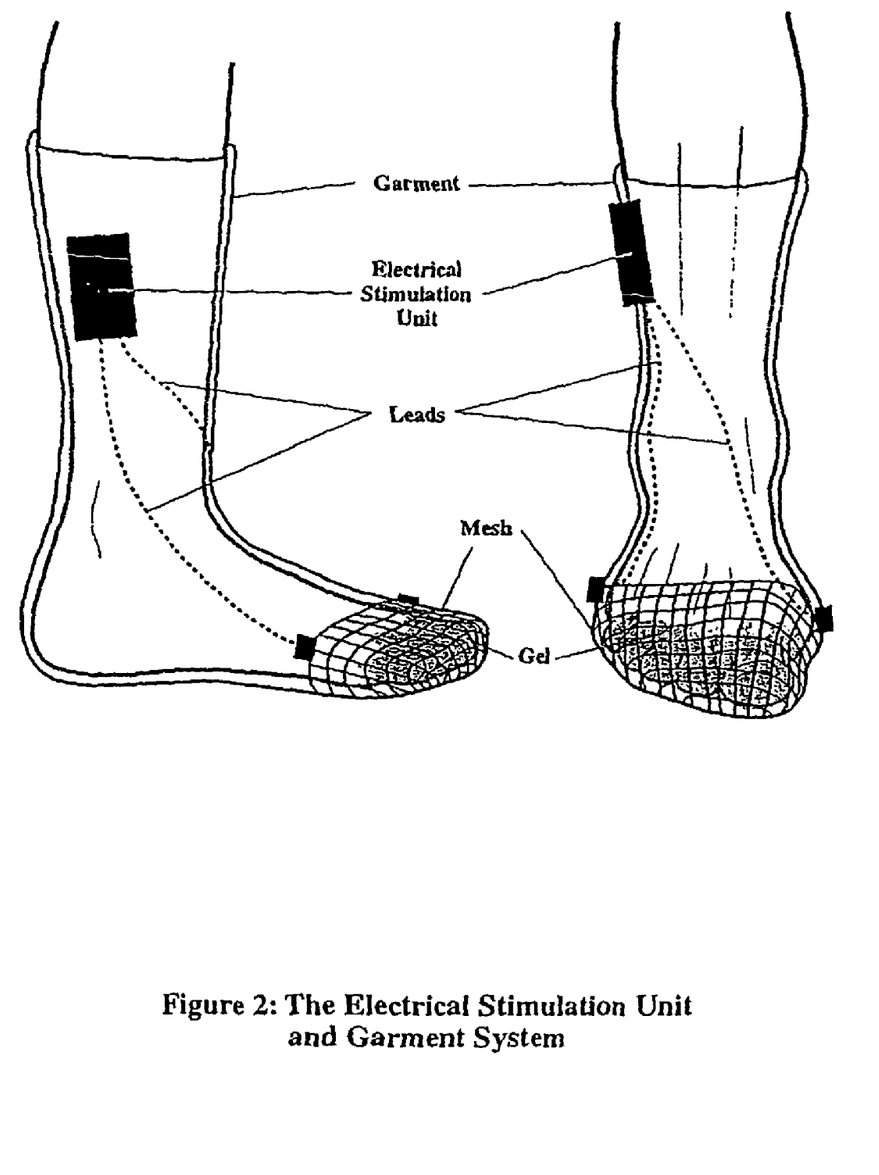
FIG. 2 shows an apparatus or apparel that allows for treatment of an infected area by contacting the infected area with an aqueous solution providing a direct current to the aqueous solution across the infected area.

Referring now to the drawings, and, more particularly, to FIG. 2 thereof, the apparatus can be adapted to for wearing or attachment to a subject. The apparatus includes a (1) membrane made of a material that is impervious to aqueous solutions, filled with an aqueous solution (2) in contact with an infected area of a subject. The edge or periphery of the membrane may have an adhesive disposed on said edge of the membrane to provide a seal in order to prevent the aqueous solution from leaking. The apparatus includes two electrodes (3) affixed to the membrane, connected by leads (4) to a circuit (5) for providing current the aqueous solution (2) to treat the infected area. This wearable apparatus may be a sock, Apparel like devices can be used to treat the fungal infection by providing a wearable fluid reservoir to the area to be treated which also incorporates a first electrode means and a second electrode means. In some instances, this device could have the general form of a bandage or the like with an adhesive portion along the periphery of the reservoir means to provide a seal with the contact area to be treated. Then, a DC power source can be hooked up to the first and second electrode to provide the electronic field across the electrodes and the surface to be treated. This "bandage" like apparatus allows the treatment method to be undertaken without limiting the activity of the patient. A person being treated with such an apparatus will be able to be active during treatment and will hence be more likely to participate in complete treatment regimens.

Those skilled in the art will recognize that besides patches, a localized reservoir similar to the "bandage" reservoir means can be made into part of a piece of apparel. Depending upon the sites of the fungal infection the apparel could be in the form of a sock, sweat-pant, or shirt.

EXAMPLE 3

It has also been found that certain additives to the aqueous solution in the reservoir can increase the efficacy of the treatment regimen. For instance, it has been found that an oxygenating source such as hydrogen peroxide accelerates the reduction of onchymycotis. Preferably the concentration of hydrogen peroxide is in the range of 0.01 to about 2 weight percent. The solution at those concentrations can be pre-prepared, or can be freshly prepared just prior to treatment. Solution can also be adjusted for slat concentration so that they are isotonic, and additionally buffer systems can be added so that the pH of the solutions remains close to physiological conditions of the tissue being treated.

EXAMPLE 4

In order to demonstrate the efficacy of direct current from a low voltage source (LVDC) or electrostimulation (E-stim) as an antifungal agent for clinical use in the treatment of onychomycosis pure cultures of *Trichophyton rubrum* and *Trichophyton mentagrophytes* grown on a solid agar medium were subjected to clinically relevant doses of LVDC. To determine antifungal effects due to germicidal and/or fungistatic activity of LVDC, the diameters of any zones in the agar around the electrodes which lacked fungal growth after E-stim were measured and compared to control cultures.

Zones devoid of fungal growth were observed for both *Trichophyton rubrum* and *Trichophyton mentagrophytes* around both the anode and cathode when clinically relevant doses of LVDC from 500 microamperes to 3 milliamperes were applied. In this dose range, LVDC acted fungicidally in a dose dependent manner.

During the past ten years, new treatment protocols which employ electrical stimulation (E-stim) have begun to be used in the treatment of certain types of wounds. The clinical efficacy of such treatment is now well documented. One of the ways in which E-stim probably plays a role in enhancing wound healing is by its antimicrobial effect. Several in vitro studies have conclusively demonstrated that E-stim application is antibacterial to most of the pathogenic bacteria commonly found in wounds. In the course of clinical use of low voltage direct current electrostimulation (LVDC E-stim) in wound treatment during the last 10 years, it became evident that, in addition to its enhancement of the would healing process, E-stim also seemed to significantly ameliorate many cases of onychomycosis of the toenail. Subsequently, regular employment of this modality in the treatment of onychomycosis resulted in clinical success.

In order to begin determining the factors responsible for the observed efficacy of this modality in the treatment of onychomycosis, in vitro experiments were conducted to evaluate the antifungal effects of LVDC E-stim in the control and/or eradication of the two primary etiologies of onychomycosis, *T. rubrum* and *T. mentagrophytes*. LVDC E-stim is clinically significant in the treatment of onychomycosis in conjunction with or alternative to other current therapies.

Materials and Methods

Organisms:

The medium employed to culture all fungi was Sabouraud Dextrose Agar (SDA) in 100 ml petri plates obtained from Becton Dickinson Microbiology Systems. (Becton Dickinson Microbiology Systems, PO Box 243, Cockeysville, N. Mex. 21030). Pure cultures of the dermatophyte fungi *T. rubrum* and *T. mentagrophytes* were obtained from Presque Isle Culturest. Permanent stock cultures of *T. rubrum* were established by inoculation of the organism onto a solid growth medium consisting of SDA in petri plates, and subsequent incubation of these SDA plates at 25° C. for 7 days. After this time period, each SDA plate was covered by numerous colonies of *T. rubrum* which had coalesced into a homogeneous, fluffy fungal "lawn" (or continuous mass of growth) along the entire surface of the agar. Permanent stock cultures of *T. mentagrophytes* were established in the manner described above for *T. rubrum*. The stock cultures of both fungi were maintained at 4° C. for the entire time period of these experiments and were weekly monitored for viability.

Experimental Procedure and Instrumentation:

All of the LVDC E-stim experiments described in this report were performed in a NUAIRE Class 11, Type A/B3 biological safety cabinet using standard aseptic techniques. All LVDC E-stim was performed using a Rich-Mar VI LIDC Stimulator. Independent current readings were made with a BK Precision amp-meter from I Dynascon Corporation.

For each E-stim experiment, a 1.0 cm section of agar containing either *T. rubrum* or *T. mentagrophytes* growing on the surface was removed aseptically from the respective SDA stock culture plates using a sterile dissecting needle. The 1.0 CM2 piece of SDA containing either *T. rubrum* or *T. mentagrophytes* was then transferred to 5 ml of sterile 0.9% saline. The sterile saline tube was mixed by vortexing for 10 sec in order to dislodge the fungal hyphae, conidia and spores from the surface of the agar. Using a sterile micropipeter, 250 ml of the fungal-saline solution were transferred to a new, sterile SDA petri plate. If multiple SDA plates were to be inoculated in a given experiment, this procedure was performed multiple times from the same fungal-saline solution. The fungal-saline solution was evenly distributed over the entire surface of each of the inoculated SDA plate(s) using a sterile glass spreading rod. The SDA plates were then incubated at 25° C. for 24 hr. At the end of this period, a barely visible film of fungal growth covered the entire growth medium surface of the SDA plates. Non inoculated control SDA plates were included in each experimental group to insure the sterility of the medium.

After 24 hr of incubation, electrical current was applied to each experimental SDA plate containing either *T. rubrum* or *T. mentagrophytes* by a Rich Mar VI LIDC Stimulator. The electrodes used to accomplish this consisted of 2 pieces of stainless steel (1 mm diameter and 2.5 cm long) which were permanently inserted through the top portion of a sterile petri plate 1.9 cm apart from each other, and which were secured with epoxy cement on the outer surface. The electrodes were disinfected and stored in 95% ethanol prior to and between experiments. Just prior to each experiment, the top portion containing the electrodes was removed from the 95% ethanol storage unit, the ethanol was allowed to evaporate, and the electrodes were inserted into the agar of the bottom portion of a SDA plate containing 24 hr growth of either fungus by closing the top portion over the lower portion of a petri plate. Then, either the electrodes remained in the agar for 30 min at room temperature (22-24° C.) without LVDC application (0 amperes), or LVDC was applied using the E-stim apparatus described above. A current of either 500 microamperes, 1 milliamperes, 2 milliamperes or 3 milliamperes LVDC was applied for 30 minutes at room temperature (22-24° C.). All amperages were confirmed by the use of an independent amp-meter connected in series. In each experiment, in order to confirm fungal viability and media soundness, a control SDA plate containing the particular fungus used in the experiment, but which was not subjected to either E-stim or electrode intrusion, was also included. This plate was inoculated at the same time, in the same manner and from the same saline tube as the experimental plates.

After LVDC E-stim, each SDA petri plate was incubated at 25° C. for 24 hr to allow for additional fungal growth which could then be easily visualized. Following this 24 hr incubation, the diameter of any zones lacking fungal growth (where no additional fungal growth occurred after application of E-stim) at the location of both the positive and negative electrodes was measured to the nearest 0.1 mm using a millimeter ruler and a dissecting microscope. The SDA plates were then incubated for an additional 3 to 5 days, with additional observations and measurements made daily.

To determine if the electrode material itself was toxic to either of the two fungi, or if any ethanol (used in disinfection) remained on the electrodes during the E-stim application (which might kill the fungus or inhibit its growth), SDA plates were inoculated with either *T. rubrum* or *T. mentagrophytes* and incubated for 24 hr as described above. Following this, the electrodes were inserted into the SDA plate containing either of the fungi and allowed to remain for 30 minutes (as previously described), but no electric current was applied (0 amperes). The SDA plates were then incubated for 7 days as described previously, and then checked for the presence of any zones lacking fungal growth during each of these seven days.

To determine if any toxic or inhibitory antifungal metabolites were generated in the SDA growth medium as a result of the application of electric current, LVDC of either 3 or 8 milliamperes was applied to a SDA plates (as described) for 30 min prior to inoculation of either *T. rubrum* or *T. mentagrophytes*. Immediately following this, 250 microliter of fungal-saline solution of either *T. rubrum* or *T. mentagrophytes* was evenly distributed overeat surface as described previously. The SDA plates were then incubated at 25° C. for 7 days, and the presence of any zones lacking fungal growth near the site of the electrode contacts (or elsewhere) was observed and/or measured each day.

To determine if LVDC E-stim is acting primarily in a fungistatic manner (inhibited fungal growth but did not kill fungal cells) or a fungicidal manner (killed fungal cells), the following was done during each experiment with either *T. rubrum* or *T. mentagrophytes*. LVDC E-stim was applied as described above, and after 24 hr incubation at 25° C., samplings were carefully taken in the areas lacking fungal growth around each electrode with a sterile swab in order to determine if viable fungal cells were present in these zones. This swab was then used to inoculate fresh, sterile SDA plates. These plates were incubated for 7 days at 25° C. and daily observed for the presence of any fungal growth that would result from the transfer of any viable fungal hyphae or spores from an experimental plate to the new SDA plate. A control plate inoculated with fungi taken from the same experimental plate, but from a region away from the electrodes and containing fungal growth, was also included with each of these experiments.

Results:

In this investigation, several clinically relevant doses of LVDC E-stim were applied to 24 hr pure cultures of *T. rubrum* or *T. mentagrophytes* growing on SDA plates. Following this, the diameter of any zones around each electrode lacking fungal growth were observed and measured. For each fungus, each experiment was replicated three times at the specified current and time settings. The size of the zones around each electrode that lacked fungal growth for *T. rubrum* or *T mentagrophyte* due to the application of LVDC E-stim at the various amperages used. For all amperages except 0 amperes, circular or roughly circular zones devoid of fungal growth were observed around both the positive (anode) and negative (cathode) electrodes. In addition, we observed an increase in the diameter of the zones with increasing amperages for both fungi (FIG. 1). Because we inserted 1 mm electrodes into the semi-solid agar surface during each experiment in order to generate a current, there was a depression produced in the agar surface at the location of these electrodes on all SDA plates. This was due, most likely, to compression and/or liquefaction of the agar. Consequently, the absence of growth observed directly under each electrode in this study, as noted in a previous was not considered to be indicative of fungicidal or fungistatic activity.

In order to confirm that the antifungal effects on *T. rubrum* and *T. mentagrophytes* observed in this study were due to the application of LVDC E-stim and not to other possible causes, the following controls were done. To rule out the possibility that the observed antifungal effects were due to the electrode material itself, in each round of experiments, a SDA plate was inoculated with either fungus and incubated for 24 hr. After this, the electrodes were inserted in the same manner and for the same time period as we would in a typical experiment using LVDC, but no current was applied (0 amperage). The plates were then incubated and observed as described above. On these SDA plates, no areas devoid of fungal growth around either electrode were ever observed with either *T. rubrum* or *T. mentagrophytes*. This same experiment was also used to determine if the lack of fungal growth around the two electrodes was due to any remaining ethanol (used to disinfect the electrodes between experiments) on the electrodes. If this were the case, some area devoid of fungal growth should have been observed around the region where the electrodes were inserted into the agar plates, even without the application of LVDC (0 amperes). No such region was observed.

Another possible reason for the antifungal effects observed in this investigation was that changes produced in the fungal growth medium (SDA) as a result of LVDC E-stim application made the medium no longer supportive of fungal growth.

To investigate this possibility we did the following set of experiments. Prior to the inoculation of either fungus onto the SDA medium, LVDC of either 3 milliamperes (the highest clinical amperage used in this study) or 8 milliamperes (beyond the clinical range used) was applied to 8 SDA plates for 30 min each (4 plates at 3 milliamperes, and 4 plates at 8 milliamperes). *T. rubrum* was then inoculated on 2 of the 3 milliampere and 2 of the 8 milliampere plates and incubated for 7 days. *T. mentagrophytes* was inoculated similarly. If the medium was indeed changed by LVDC E-stim application in such a way as to prevent or inhibit fungal growth, this should be observed as a lack of growth in the agar in the region around the electrodes (or possibly some other region of the agar). No such region lacking fungal growth was observed for either *T. rubrum* or *T. mentagrophytes* in the areas surrounding either of the electrodes (or any other area) when we inoculated the fungi onto a SDA plate after 3 milliamperes of LVDC application. At 8 milliamperes, no region lacking fungal growth was observed for either fungus at the cathode. However, at this amperage, some discoloration, liquefaction and subsequent depression of the agar was observed in the area in which the anode was placed. Neither fungus was able to grow very well over this discolored, depressed anode region at 8 milliamperes. Otherwise, growth occurred throughout the remainder of the plate.

In order to determine if the range of LVDC E-stim application used in these experiments was acting primarily as an fungicidal agent or fungistatic agent, the areas around each electrode that lacked fungal growth were sampled with a sterile swab 24 hr after E-stim application for the presence of viable fungal cells or spores. A total of 24 samplings for *T. rubrum* and 24 samplings for *T. mentagrophytes* were made. A sampling was taken from the area around each electrode on all plates which received a dose of 500 microamperes, 1 milliampere, 2 milliamperes and 3 milliamperes. Growth was observed on the fresh SDA plates inoculated with a swab after sampling an experimental plate. In the remaining 22 samplings, no growth was observed.

Finally, as has previously been reported, the production of gas bubbles at the cathode during all experiments, and occasionally, also at the anode was observed. In addition, a blue discoloration was observed around the cathode, possible due to a pH change.

Discussion:

This investigation was undertaken in order to determine if the clinically observed efficacy of LVDC E-stim in the treatment of onychomycosis is due (at least in part) to an antifungal effect of the modality. Antibacterial effects against many of the common bacterial wound pathogens have been demonstrated in vitro for both low voltage direct current and high voltage pulsed current in several studies. However, such in vitro documentation is negligible with respect to the effect of electric current on the common fungal pathogens, the yeast *Candida albicans* being one of the few exceptions. Clinically relevant doses of LVDC E-stim are antifungal in vitro to the two primary causes of onychomycosis, the fungi *T. rubrum* and *T. mentagrophytes*. The antifungal effects of LVDC E-stim occur in a dose dependent manner in the clinically relevant ranges used (500 microamperes to 3 milliamperes) in these in vitro experiments.

A second and related determination to be made was whether LVDC E-stim in the dose range used was acting primarily as a fungistatic agents or a fungicidal agent. To determine this, the areas devoid of fungal growth around the electrodes in each experiment were carefully sampled with a sterile swab 24 hr after E-stim to assay for any viable fungal cells or spores which could give rise to fungal colonies on new SDA plates. Similar methodologies have been used to determine if E-stim is bactericidal or bacteriostatic. In 46 of the total of 48 samplings, no fungal growth was observed on the newly inoculated SDA plates. The two plates that did show some growth were both from the cathode region of the 3 milliampere dose plate. These zones had the largest diameter, and it is possible that the sampling swab may have inadvertently touched some viable fungal cells at the periphery of the zone. As such, they would represent an artifact of these experiments, rather than actual lack of fungicidal activity, which is likely the case. Consequently, the data strongly suggest that LVDC E-stim is acting fungicidally in the amperage range used in this study.

Cellular death can be brought about by a number of factors that include: damage or denaturation of key cellular enzymes; damage to DNA; damage or disruption of the cell membrane; damage or destruction of key cellular transport systems. Electricity is believed to most likely kill cells by affecting the molecular structure of the cell membrane, leading to fatal changes in cell membrane permeability. Such cell membrane damage could explain the antifungal effects of LVDC E-stim observed both in vivo and in vitro. However, other factors might also play a role. Application of electric current to the agar medium can result in changes in the pH of the medium, increases in temperature and the generation of toxic metabolites. All of these (and possibly others still) could act antimicrobially to one degree or another. Such factors have been considered in other studies looking at the antibacterial effects of electricity. These factors were not individually examined in this study which was mainly concerned with determining if LVDC E-stim application itself was antifungal. If the application of electricity to a fungus growing on a toenail or agar surface results in the death of all or some of those fungal cells, then whether that fungicidal activity was due to fatal changes in the cell membrane of fungal cells and also to changes in pH or increases in cellular temperature is secondary to the present interest. Such aspects will hopefully be addressed in subsequent investigations.

However, this present investigation sought to demonstrate that any antifungal effects of LVDC E-stim on the two major etiologies of onychomycosis were due to the application of E-stim itself (due to the effects of electrical current), and not due to any artifacts produced as a result of our experimental methodology. Because no fungal inhibition was observed around either electrode during any trial when the electrodes were inserted but when current was not applied (0 amperes), the electrode material itself (stainless steel) is not likely antifungal. Another concern was that some of the ethanol, used to disinfect the electrodes before and in between experiments, might remain on the electrodes upon insertion into the SDA medium. Since ethanol is a disinfectant, it can kill and or inhibit fungal and bacterial cells. Thus, areas around each electrode lacking fungal growth may be due to the disinfection action of ethanol, rather than the antifungal effects of the LVDC E-stim. To minimize the possibility of this, after removal of the electrodes from their ethanol storage unit (stored in a biological hood), they were allowed to dry for a minimum of 30 seconds before they were inserted into any SDA experimental plates. No anti-fungal activity was observed at the 0 amperage setting as described above, and insufficient (or no) ethanol remained on the electrodes upon insertion into any SDA plate. It is clear that all the ethanol had evaporated and was not a cause of the observed zones lacking fungal growth.

Another possible reason for any observed areas lacking fungal growth around either electrode was that the application of LVDC E-stim in the current range changed the SDA medium in some way so that is could no longer support the growth of either *T. rubrum* or *T. mentagrophytes*. This could result from the production of toxic and or inhibitory products in the medium as a result of the LVDC application, or from changes in the pH of the medium due to LVDC, or from the denaturation and degeneration of necessary nutrients in the medium without which the fungi could not grow. To investigate this possibility, either 3 milliamperes or 8 milliamperes of LVDC E-stim was applied to several SDA plates before they were inoculated with either *T. rubrum* or *T. mentagrophytes*. If the SDA medium was indeed changed by LVDC application so that it now prevented or inhibited fungal growth, this should be observed as a lack of growth in/on the agar in the region(s) around the electrodes (or possibly some other region of the agar). As the data show, no such region was observed at 3 milliamperes around either the cathode or the anode, or anywhere else on the plates. Growth occurred throughout each SDA plate. At 8 milliamperes, more than twice the highest amperage used in this study, growth occurred at the cathode, but not the anode, where liquefaction and depression was observed. It is probable that at this amperage, lack of growth was due to some physical changes produced in the medium (i.e., liquefaction), or to the generation of toxic metabolites, or the denaturation of vital nutrients, or a combination of several factors. However, because 3 milliamperes was the highest dose of LVDC E-stim used in these antifungal studies, at this amperage and at the lower amperages, the media was not altered in a significant way so as to negatively affect the growth of either fungus. To further support this assertion, in the experiments involving 500 microamperes, 1 milliampere, 2 milliamperes and 3 milliamperes of LVDC E-stim, the areas of the agar lacking fungal growth due to the LVDC application were still capable of supporting the growth of both fungi. This is evidenced by the fact that if these agar plates were incubated at 25° C. for 7 to 10 days, eventually viable fungi from outside the diameter of the fungicidal zone would clearly begin to re-colonize that zone until a solid fungal lawn was again formed over the entire area. Together, these results strongly support the assertion that any possible changes produced in the SDA medium were not responsible for the observed zones lacking fungal growth around the electrodes in the clinically relevant dose range of LVDC that we employed in this study.

EXAMPLE 5

Similar to LVDC discussed in Example 4, monophasic pulsed current from a high voltage pulsed source(HVPC) may also be used as another preferred embodiment of this invention. For HVPC, the direct current is supplied by a voltage source of less than about 150 volts.

Therefore, while several preferred forms of the inventive method and apparatus have been shown and described, and several modifications thereof discussed, persons skilled in this art will readily appreciate that various additional changes and modifications may be made without departing from the spirit of the invention, as defined and differentiated by the following claims.

What is claimed is:

1. An apparatus for providing an antifungal agent for treating a fungal infection of a nail, the apparatus comprising:
   a footbath comprising a first electrode and a second electrode and configured to receive an aqueous solution, the footbath configured to permit placement of the nail infected with the fungal infection in the aqueous solution;
   and
   a current source coupled to each of the first electrode and the second electrode and configured to provide a pulsed current as the antifungal agent to the aqueous solution to thereby treat the fungal infection of the nail, the pulsed current being provided by the source being a voltage of less than 150 volts, a monophasic waveform with pulse pairs having intervals of 150-330 microseconds, a pulse width of 5-50 microseconds, and a pulse repetition frequency of 100-200 Hz.

2. The apparatus set forth in claim 1 wherein said first electrode and second electrode each comprise stainless steel.

3. An apparatus for treating a fungal infection of a nail, the apparatus comprising:
   a footbath comprising a first electrode and a second electrode and configured to receive an aqueous solution, the footbath further configured to permit placement of the nail infected with the fungal infection in the aqueous solution; and
   a current source coupled to each of the first electrode and the second electrode and configured to provide a pulsed current to said aqueous solution at a fungicidal or fungistatic amount to thereby treat the fungal infection of the nail, the pulsed current being provided by the source being a voltage of less than 150 volts, a monophasic waveform with pulse pairs having intervals of 150-330 microseconds, a pulse width of 5-50 microseconds, and a pulse repetition frequency of 100-200 Hz.

4. The apparatus set forth in claim 3 wherein said first electrode and second electrode each comprise stainless steel.

5. The apparatus of claim 1 wherein said apparatus is further constructed and arranged to treat the infected area on the skin of the foot. .

6. The apparatus of claim 1 further comprising an aqueous solution that includes hydrogen peroxide.

7. The apparatus of claim 6 wherein said aqueous solution comprises about 0.01 to about 3.0 weight percent hydrogen peroxide.

8. An apparatus for providing an antifungal agent for treating a fungal infection of a nail of a foot, the apparatus comprising:
   a footbath comprising a fluid reservoir comprising an aqueous solution, the fluid reservoir comprising a front wall, side walls and a back wall, in which each of the front wall, the side walls and the back wall are coupled to a bottom surface, the front wall, side walls, back wall, and bottom surface being sized and arranged as the footbath to receive the one or both feet, the front wall comprising a first electrode so that when the foot is placed in the fluid reservoir the first electrode is positioned in close proximity to at least one toe of the foot, and the fluid reservoir further comprising at least a second electrode on one of the sidewalls, back wall or bottom surface so that the second electrode is positioned in close proximity to the heel of the foot; and
   a current source coupled to each of the first electrode and the second electrode and configured to provide a pulsed current as the antifungal agent to said aqueous solution in the footbath at a fungicidal or fungistatic amount to thereby treat the fungal infection of the nail, the pulsed current being provided by the source being a voltage of less than 150 volts, a monophasic waveform with pulse pairs having intervals of 150-330 microseconds, a pulse width of 5-50 microseconds, and a pulse repetition frequency of 100-200 Hz.

* * * * *